United States Patent
Sifers et al.

[11] Patent Number: 5,323,992
[45] Date of Patent: Jun. 28, 1994

[54] TUBE HOLDING DEVICE

[76] Inventors: Lorna L. Sifers, Box 193, Drake, Colo. 80515; Robin J. Pasquarosa, 520 Redwood Cir., Berthoud, Colo. 80513

[21] Appl. No.: 835,130

[22] Filed: Feb. 12, 1992

[51] Int. Cl.$^5$ ............................................. A47G 1/17
[52] U.S. Cl. ................................... 248/205.3; 248/65; 24/129 R
[58] Field of Search ............... 248/205.3, 79, 65, 74.1, 248/74.2, 73; 24/129 R, 129 D, 130

[56] References Cited

U.S. PATENT DOCUMENTS

| | | | |
|---|---|---|---|
| 1,660,829 | 2/1928 | Burd | 24/129 R |
| 3,363,864 | 1/1968 | Olgreen | 248/74.2 X |
| 3,630,195 | 12/1971 | Santomieri | 248/74.2 X |
| 4,039,744 | 8/1977 | Seaquist | 248/65 X |
| 4,901,960 | 2/1990 | Gary | 248/205.3 |
| 4,910,362 | 3/1990 | Kinner | 24/129 R X |
| 5,102,399 | 4/1992 | Chu | 248/205.3 X |

*Primary Examiner*—Ramon O. Ramirez
*Attorney, Agent, or Firm*—Dean P. Edmundson

[57] ABSTRACT

A tube holder for detachably holding and supporting a flexible tube (e.g., an oxygen tube). The holder includes a base, a plurality of upright retention fingers supported by the base, and preferably a pressure-sensitive adhesive layer for attaching the holder to the skin of a patient, for example. The holder safely supports and retains the tube in a desired position. When desired, the tube can be detached from the holder without detaching the holder from the skin.

8 Claims, 2 Drawing Sheets

TUBE HOLDING DEVICE

FIELD OF THE INVENTION

This invention relates to holding devices and systems. More particularly, this invention relates to devices and systems for holding and retaining oxygen tubes.

BACKGROUND OF THE INVENTION

Patients who are required to receive oxygen typically do so through a supply tube which is flexible and which extends from a source of oxygen (e.g., a tank) to the patient. The tube is normally attached to a nose cannula for use by the patient.

The oxygen tube is often extended rearwardly from the nose cannula and may extend over the ears, around the back of the head, or both. Sometimes the oxygen tube is clipped or clamped to a pillow bed or frame, if the patient is bed-ridden.

Adhesive tape has also been used to hold oxygen tubing onto the cheeks of infants requiring oxygen. The tape is criss-crossed around the tubing and then applied to the cheek area. Tape is used in the same manner to hold IV tubing, gastro-intestinal tubes and catheters onto the skin. However, there are a number of disadvantages associated with the use of adhesive tape. For example, in order to remove or replace the tubing it is necessary to remove the tape from the skin of the patient. This is irritating to the skin because each time the tape is removed it causes a stripping of the epidermis which over time will cause an abraded area which is painful and a potential source of infection. Furthermore, not all tapes are waterproof and may not stay in place when the skin is washed. Also, some patients with oily or perspiring skin will require more frequent re-applications of adhesive tape because of ineffective adhesive properties which do not hold on wet or oily skin.

Semi-permeable plastic adhesive dressings have been used primarily to secure IV tubing to patient's skin. Although such dressings hold the tubing very securely, they must be removed and discarded each time the tubing is removed or must be changed. Such dressings are difficult to remove and apply because they are extremely thin and they have a tendency to stick to themselves. Furthermore, these dressings can be very irritating to the skin if they are removed several times per day. They are also very expensive. With most premature infants, removal of the tubing commonly occurs 3 or 4 times in an eight hour shift.

Although it is possible to use a stomadhesive skin barrier as a base to which tubing can be attached, this also involves certain disadvantages. For example, adhesive tape must be used to attach the tubing to the base. Because of the small size of infants, the skin barrier must be one inch or less in diameter. This small size makes it difficult to attach the tubing to the skin barrier with adhesive tape. As a result, the tubing may not be held in place as securely as necessary or desired.

Although some of the previous holders and clamps may be satisfactory for certain types of patients, such devices are generally not wholly satisfactory or convenient for use by infants, small children, or patients of impaired mental faculties.

Neonatal intensive care units composed of high risk premature infants which may weigh less than two pounds and full term infants with birth defects or congenital anomalies frequently require supplemental oxygen and countless other procedures which are both costly and time consuming. Clinicians do not have the time for re-taping the tubing 3 to 5 times per shift or having another staff person to help hold the infant while applying the dressing. Furthermore, hospitals cannot afford the costs of the required products. The number of high-risk infants increases each year.

There has not heretofore been provided an effective and safe tube holder which can be easily used by all types of patients and which does not harm the skin of the patient.

SUMMARY OF THE PRESENT INVENTION

In accordance with the present invention there is provided a tube holder for detachably holding and supporting a flexible tube. In one embodiment the holder comprises:

(a) a base member;

(b) a plurality of spaced-apart upright retention members supported by the base member; and (c) attachment means carried by the base member for attaching the base member to a desired surface. The upright retention members cooperate with each other to grip and retain the tubing. The attachment means preferably comprises a pressure-sensitive adhesive which enables the base member to be removably attached to a desired surface, e.g., human skin.

Previously used materials must be removed at the same time the tubing is removed, and a new replacement piece must be used to re-attach the tubing in order to secure the tubing properly.

The tube holder of this invention can remain in place on the skin for several days (e.g., 5 days) while still allowing the care provider to replace and re-attach the tubing as often as necessary. It does not cause skin irritation, and it is easy to apply (i.e., one person can do so easily). Also, the holder will stay in place when the patient is perspiring or has oily skin, so long as the skin is cleaned prior to the application of the holder to the skin.

Use of the holder of this invention is very economical because it can be used for several days before being replaced. It is also a time-saver for medical staff because it allows them to spend more time on other procedures rather than re-taping tubing several times per shift. The holder of this invention provides comfort and simplicity of attachment. Because it also saves time in use and does not have to be replaced very often, it is very cost effective.

BRIEF DESCRIPTION OF THE DRAWINGS

The invention is described in more detail hereinafter with reference to the accompanying drawings, wherein like reference characters refer to the same parts throughout the several vies and in which.

DETAILED DESCRIPTION OF THE INVENTION

Figure 1:
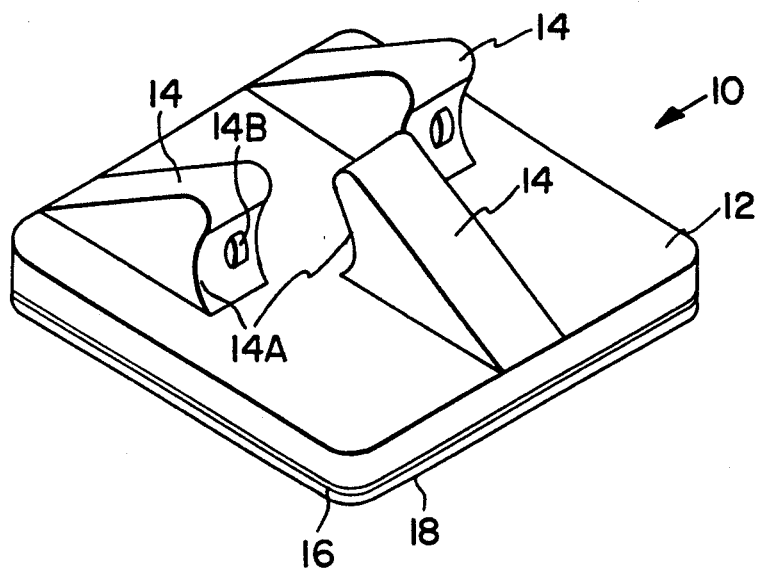
FIG. 1 is a perspective view of one embodiment of tube holder of the invention.
Figure 2:
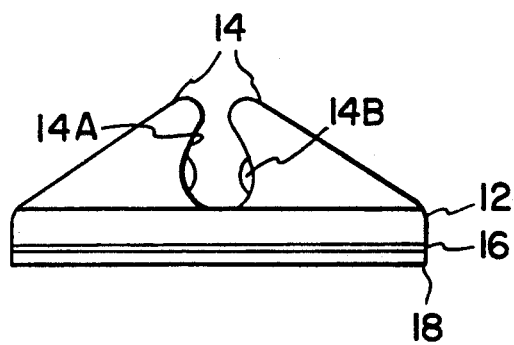
FIG. 2 is a front elevational view of the holder of FIG. 1.

In FIGS. 1 and 2 there is illustrated one embodiment of tube holder 10 of the invention comprising a base member 12 and upright spaced-apart retention members 14 secured to the upper surface of the base member. Carried by the lower surface of the base member is a layer 16 of pressure-sensitive adhesive. Covering the adhesive layer is a removable protective sheet or layer 18.

The upright retention members are positioned such that they can cooperate with each other to grip and retain an oxygen tube between them. Preferably the retention members include a somewhat concave surface 14A for accommodating the external surface of the tube to be held and retained. It is also preferred for the retention members to be arranged on the upper surface of the base in a manner such that at least two retention members oppose each other, as illustrated in FIG. 1. Opposing retention members may also be staggered, as illustrated. There are at least two retention members on the base.

The height of the retention members may vary, so long as they have a height greater than the diameter of the tube to be held and retained. For example, the diameter of the tube to be held may vary from about 0.06 inch to 0.25 inch. The height of the retention members may vary from about 0.1 to 0.4 inch (preferably about 0.25 inch). The spacing between the retention members may also vary. The width of each retention member may also vary. Preferably the width is about 0.125 inch.

Also, the dimensions and shape of the base member may vary. Typically the base member is square, rectangular, circular, or oval. The length and width may be as small as about 0.5 inch or as large as about one inch.

If desired, the concave face of each retention member may include a rib or projection 14B to facilitate gripping of the tube to be held. The size and shape of the rib may vary.

The base member and the retention members are preferably integral and are also preferably composed of plastic. Suitable plastics include, for example, both rigid and flexible plastics. Various useful plastics include silicone, fluorosilicone, latex rubber, polyvinylchloride, polycarbonate, polypropylene, polyurethane, acetal resin, cflex resin, polyethylene terephthalate, thermoplastic elastomers, nylon, polysulfone, polyaryletherketone, polyesters, etc. Preferably the plastic selected exhibits chemical resistance to solvents and is also non-allergenic. It is presently preferred to use a soft and flexible plastic or rubber material.

The adhesive which is used may be any suitable hypoallergenic adhesive of the type previously used in medical applications. For example, useful adhesives include carboxymethylcellulose polymers and copolymers. A commercially available adhesive which is useful is Convatec Extra Thin. It is available as a semi-clear wafer with good adhesion to the skin.

Figure 3:
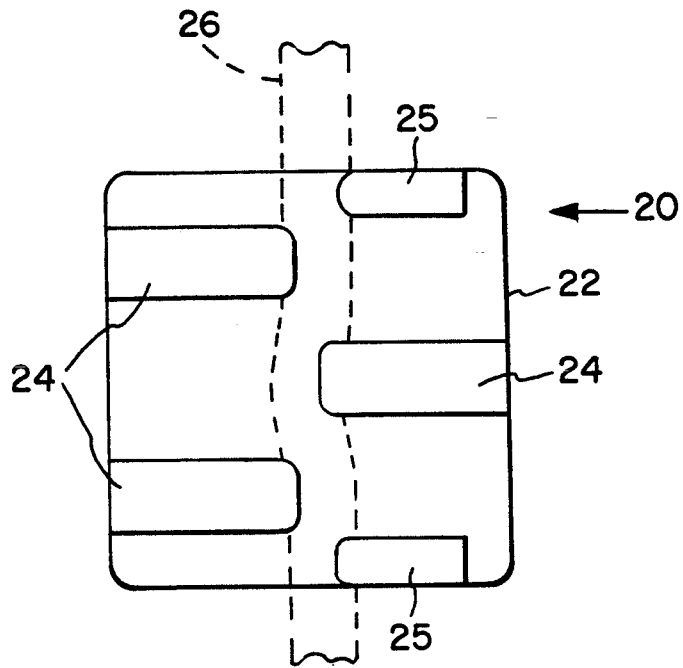
FIG. 3 is a top plan view of another embodiment of tube holder of the invention.
Figure 4:
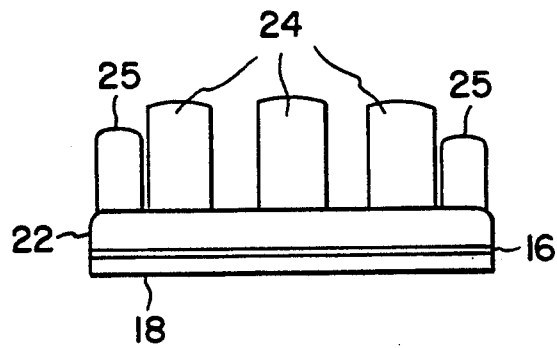
FIG. 4 is a side elevational view of the holder shown in FIG. 3.
Figure 5:
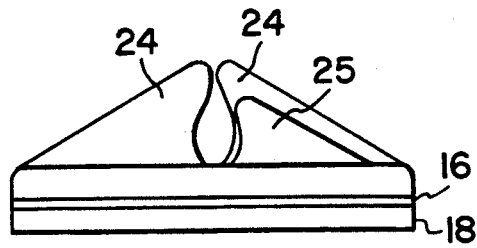
FIG. 5 is a front elevational view of the holder shown in FIG. 3.

FIGS. 3-5 illustrate another embodiment of tube holder 20 of the invention comprising base member 22 and upright retention members 24 and 25 for gripping and retaining a tube 26. In this embodiment there are three tall retention members 24 and two shorter retention members 25. The use of more retention members in this embodiment than in the embodiment shown in FIGS. 1 and 2 results in more secure holding of the tube.

Use of the holder of this invention enables a flexible tube to be easily and readily attached to and supported by the holder. The adhesive layer enables the holder to be firmly and safely attached to the skin of the patient (even to the skin of infants) for longer periods of time than is possible using conventional adhesive tape or other conventional dressing materials.

A further advantage of the holder of the invention is that the tubing is securely retained and supported by the holder, and yet the tubing can be pulled loose from the holder without damage in the event that the tubing should become entangled or caught on an obstruction. Also, if an infant's hand should become entangled in the tubing, the tubing can be pulled loose from the holder without damaging the holder and without pulling the holder loose from the skin.

Other variants are possible without departing from the scope of this invention.

What is claimed is:

1. A tube holder for detachably holding and supporting a flexible tube, said holder comprising:
   (a) a base member;
   (b) a plurality of spaced-apart upright retention members supported by said base member; wherein said retention members comprise at least three upwardly-extending fingers in opposing relation, and wherein said fingers are staggered on said base member; and
   (c) attachment means carried by said base member for attaching said base member to a desired surface; wherein said base member includes a lower surface, and wherein said attachment means comprises adhesive which is carried by said lower surface.

2. A tube holder in accordance with claim 1, wherein said base member has a generally planar upper surface, and wherein said retention members are secured to said upper surface.

3. A tube holder in accordance with claim 1, wherein said base member includes a generally planar upper surface, wherein said retention members are secured to said upper surface; wherein each said finger includes a concave face, and wherein an outwardly projecting rib is carried on said concave face.

4. A tube holder in accordance with claim 1, wherein said adhesive is a pressure-sensitive adhesive.

5. A tube holder in accordance with claim 4, further comprising a release liner covering said adhesive.

6. A tube holder in accordance with claim 3, wherein each said finger has a height in the range of about 0.1 to 0.4 inch.

7. A method for detachably securing a flexible tube to a patient, the method comprising the steps of:
   (a) providing a holder comprising:
      (i) a base member having upper and lower surfaces;
      (ii) at least three upwardly-extending spaced-apart fingers secured to said upper surface of said base member in opposing relation, and wherein said fingers are staggered on said base member; and
      (iii) adhesive attachment means carried by said lower surface of said base member;
   (b) attaching said base member to said patient by means of said adhesive attachment means; and
   (c) attaching said flexible tube to said holder, wherein said tube is retained by said upwardly extending fingers.

8. A method in accordance with claim 7, wherein said attachment means comprises a pressure-sensitive adhesive.

* * * * *